United States Patent [19]

McCoy

[11] Patent Number: 5,045,104

[45] Date of Patent: Sep. 3, 1991

[54] SYNERGISTIC COMPOSITIN OF 2-(2-BROMO-2-NITROETHENYL) FURAN AND 2-BROMO-2-NITROPROPANE-1,3-DIOL AND USES THEREOF

[75] Inventor: William F. McCoy, West Lafayette, Ind.

[73] Assignee: Great Lakes Chemical Corporation, West Lafayette, Ind.

[21] Appl. No.: 565,803

[22] Filed: Aug. 9, 1990

Related U.S. Application Data

[63] Continuation-in-part of Ser. No. 205,078, Jun. 10, 1988, abandoned.

[51] Int. Cl.[5] .................... A01N 33/18; A01N 33/24; A01N 43/08
[52] U.S. Cl. ........................................ 71/67; 514/471; 514/727; 162/161; 210/764
[58] Field of Search .................... 71/67; 514/471, 727; 162/161; 210/764

[56] References Cited

U.S. PATENT DOCUMENTS 4,859,708  8/1989  Donofrio et al. .................... 514/727

OTHER PUBLICATIONS

Nazarova, "Concerning B-Nibrovinyl-5-Substituted Furans", Zhur. Cebshcski Khim., vol. 24, 1954, 589-592.
Gruntfest et al, "Physiochemical Properties and Reactivity ...", etc. Zh. Org. Kh. vol. 8, 1972, pp. 405-411.
Nazarova et al, "Synthesis of Some Furylnibroolefins with Potential Biological Activity", Potemkin Khim. Fann. Zh., vol. 6, 1972, pp. 629-632.

Primary Examiner—Richard L. Raymond
Assistant Examiner—Brian Bembenick
Attorney, Agent, or Firm—Woodard, Emhardt, Naughton, Moriarty & McNett

[57] ABSTRACT

A synergistic mixture of 2-(2 bromo-2-nitroethenyl)furan and 2-bromo-2-nitropropane-1,3-diol is disclosed. The synergistic mixture can be used as an antimicrobial in a broad spectrum of uses; the synergistic mixture is effective against bacteria, algae and fungi. An antimicrobial composition comprising the synergistic mixture and a carrier is also disclosed.

17 Claims, 1 Drawing Sheet

SYNERGISTIC COMPOSITIN OF 2-(2-BROMO-2-NITROETHENYL) FURAN AND 2-BROMO-2-NITROPROPANE-1,3-DIOL AND USES THEREOF

BACKGROUND OF THE INVENTION

1. Field of the Invention

This present invention relates to a new antimicrobial composition comprising a synergistic mixture of 2-(2-bromo-2-nitroethenyl)furan ("BNEF") and 2-bromo-2-nitropropane-1,3-diol ("BNPD") and to its uses as a broad spectrum antimicrobial agent. This application is a continuation-in-part of my copending application with Scott Thornburgh, Ser. No. 205,078 entitled "A New Industrial Antimicrobial: Uses for 2-(2-Bromo-2-nitroethenyl)-furan and a New Process for Forming 2-(2-Bromo-2-nitroethenyl)-furan" (now abandoned).

2. Description of the Art

Industrial systems generally requiring antimicrobials to control microbiological fouling include pulp and paper process waters, evaporative cooling waters, air washers, metal working fluids, wood preservatives, cosmetics, toiletries, water systems, oil field injection water and drilling needs, and institutional hard surface disinfection, and acrylic latex paints emulsions, adhesives and coatings. However, despite the many commercially available antimicrobials, not one is entirely suitable for every application due to efficacy, safety, environmental acceptability and cost.

In order to obtain antimicrobials suitable for a diversity of microorganisms found in industrial applications, combinations of antimicrobials are often used. In addition, hundreds of combinations of antimicrobials are used to prevent microorganisms from becoming less sensitive to the antimicrobial agent. Moreover, the combination of antimicrobials enables one to take advantage of many antimicrobials which have different, yet complimentary physiochemical properties. For example, the following combinations of antimicrobials are used: 2-bromo-2-nitropropane-1,3-diol and bromochlorodimethylhydantion, methylene bisthiocyanate and dodecylguanadine hydrochloride, isothiazolone and bromochlorodimethylhydantion, and 2-bromo-2-nitropropane-1, 3-diol and parabenzoio acids.

BNEF and BNPD are both useful antimiorobials. BNEF is relatively water insoluble (maximum solubility at 25° C is about 300 ppm), whereas BNPD is completely water soluble (the solubility of BNPD at 25° C is 25% (25,000 ppm)). BNEF will partition into the oil phase because it is hydrophobic, whereas BNPD is hydrophilic and will partition into the water phase. BNEF is an excellent fungicide, whereas BNPD is not. The prior art has not only failed to recognize the use of BNEF as an antimicrobial as disclosed in copending application, Ser. No. 205,078, but has also failed to recognize the combination of BNEF and BNPD. More particularly, my copending application Ser. No. 205,078 discloses the use of 2-(2-bromo-2-nitroethenyl)furan as a broad spectrum antimicrobial effective against bacteria, algae and fungi. However, this application fails to disclose a new antimicrobial composition comprising a synergistic mixture of BNEF and BNPD and its uses as a broad spectrum antimicrobial. Moreover, the prior art has failed to determine the synergistic qualities of these two antimicrobials.

In addition, the prior art has failed to recognize effective antimicrobial activity of the synergistic mixture comprising BNEF and BNPD as a broad spectrum antimicrobial.

Croshan, et. al., in an article entitled "Chemical Preservatives; Use of Bronopol as a Cosmetic Preservative", Chapter 4 of Cosmetic and Drug Preservation: Principles and Practice; (Marcel Dekker, N.Y. 1984), discloses use of 2-bromo-2-nitropropane-1,3-diol as an antimicrobial. However, Croshan, et. al. fail to disclose a new antimicrobial mixture comprising a synergistic mixture of BNEF and BNPD and is used as a broad spectrum antimicrobial of BNEF.

U.S. Pat. No. 4,859,708 ("'708 Patent") discloses a bactericidal composition and a method for inhibiting and controlling the growth of capsulated, facultative bacterium, Klebsiella pneumoniae. The composition comprises 2-bromo-2-nitropropane-1,3-diol and beta-bromo-beta-nitrostyrene. The '708 patent fails to disclose a new antimicrobial mixture comprising a synergistic mixture of BNPD and BNEF and its uses as a broad spectrum antimicrobial.

Kull, et. al. in an article entitled "Mixtures of Quaternary Ammonium Compounds and Long-chain Fatty Acids as Antifungal Agents", Applied Microbiology 9:538-541 (1961), disclose use of synergistic mixtures of quaternary ammonium compounds and long chain fatty acids as antifungal agents. Kull, et. al., fail to disclose a new antimicrobial mixture comprising a synergistic mixture of BNPD and BNEF and its uses as a broad spectrum antimicrobial.

Accordingly, a primary object of the present invention is to provide a new broad spectrum antimicrobial comprising a synergistic mixture of 2-(2-bromo-2-nitroethenyl)furan ("BNEF") and 2-bromo-2-nitropropane-1,3-diol ("BNPD").

Another object of the present invention is to provide an antimicrobial composition which exists in liquid form and comprises the synergistic mixture of BNEF and BNPD in a liquid carrier.

A still further object is to provide uses for the broad spectrum antimicrobial comprising a synergistic mixture of BNEF and BNPD.

SUMMARY OF INVENTION

The foregoing and other objects, advantages and features of the present invention may be achieved using the synergistic mixture of 2-(2-bromo-2-nitroethenyl)furan ("BNEF") and 2-bromo-2-nitropropane-1,3-diol ("BNPD") as a broad spectrum antimicrobial agent wherein the weight ratio of BNEF to BNPD is in the range of 1:1000 to 1000:1. More particularly, it has been found that the synergistic mixture of BNEF and BNPD can be used in cooling waters, pulp and paper making process flows, cooling waters, metal working fluids, air-washers, oil field injection water and drilling muds, acrylic latex paints, cosmetics, adhesives and coatings, swimming pools and spas, toiletries and other various biocide applications. The synergistic mixture is effective against a wide spectrum of bacteria, algae and fungi.

DETAILED DESCRIPTION OF THE PREFERRED EMBODIMENTS

Figure 1:
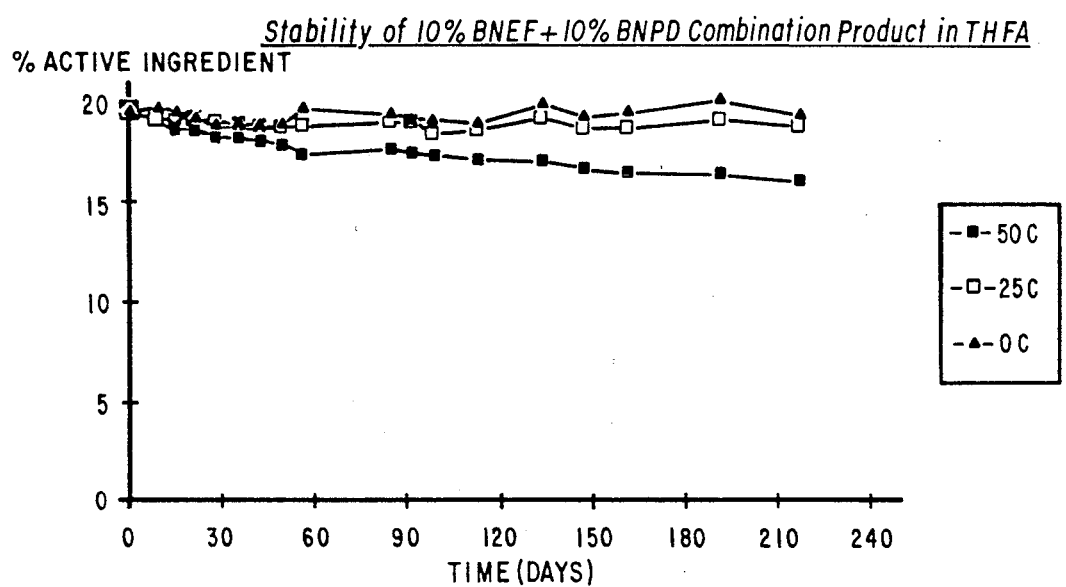
FIG. 1 is a graph showing the stability synergistic mixture of 10% BNEF and 10% BNPD in a liquid carrier.

The present invention relates to a synergistic mixture of 2-(2-bromo-2-nitroethenyl)-furan ("BNEF") and 2-bromo-2-nitropropane-1,3-diol ("BNPD"). The synergistic mixture is active against such Gram negative bacteria such as *Pseudomonas aeruginosa*, and Gram positive bacteria such a *Enterococcus faecalis, Bacillus subtilis* and *Staphylococcus aureus;* algae such as *Chlorella pyrenoidosa;* yeast such as *Candida albicans;* fungi such as *Aspergillus niger*. In addition, the synergistic mixture is effective against aerobic and anaerobic bacteria, photosynthetic bacteria, sulfate reducing bacteria, iron oxidizing bacteria and cyanobacteria.

The BNEF can be produced from furfural, an inexpensive biodegradable agricultural waste product. Preferably, BNEF can be formed according to the method set forth in my U.S. Application with Scott Thornburgh, Ser. No. 406,711, which was issued as U.S. Pat. No. 4,965,377. The BNPD can be made from formaldehyde and bromonitromethane.

The invention also relates to a novel antimicrobial composition. The antimicrobial composition which exists in liquid form comprises a synergistic mixture of BNEF and BNPD, and an inert carrier such as tetrahydrofurfuryl alcohol, dimethylformamide and N-methylpyrrolidine. The mixture comprises 20% w/v of the synergistic mixture of BNEF and BNPD and 80% w/v of carrier.

In addition, the invention relates to inhibiting microbial growth in an aqueous media by the addition of the synergistic mixture of BNEF and BNPD. Possible aqueous media include pulp and paper process waters, evaporative cooling waters, air-washers, metal working fluids, cosmetics, toiletries, latex paints and adhesives. An antimicrobially effective amount of the synergistic mixture of BNEF and BNPD is added to the aqueous media. The synergistic mixture comprises BNEF in the range of 0.5-300 ppm and BNPD in the range of 0.5-5000 ppm.

EXAMPLE

The following example is given to illustrate the process of the invention and should not be construed as limiting in scope.

The synergistic mixture can be made by dissolving BNEF and BNPD together in THFA at room temperature. Typically, the solution is 10% BNEF, 10% BNPD, and 80% THFA by weight. Any combination of active synergistic ingredient can be used but should not exceed a total concentration of more than about 40%. In other words, less than about 60% of the liquid carrier such as THFA in the mixture is not desirable. Alternatively, the antimicrobials can be added to the system to be obtained from separate solutions. In this case, the synergistic effect of the combination of BNEF and BNPD are exactly as if the two active ingredients had been added from the same solution. Typically, a 10% BNEF/90% THFA solution and a 25% BNPD/75% water solution are added from separate containers to the same system. The range for the BNEF solution in THFA is 0.5% to 40% by weight; the range for the BNPD aqueous solution is 0.5% to 25% by weight.

When BNEF and BNPD are combined, they form a synergistic mixture. Synergism refers to a case in which the performance of two or more active ingredients is improved relative to the sum of their individual performances. The method used to determine synergism follows the method disclosed by Kull et. al., "Mixtures of Quaternary Ammonium Compounds and Long-chain Fatty Acids as Antifungal Agents", *Applied Microbiology*, 9:538-541 (1961). The method defines a parameter named the "synergism index" as follows:

$$Q_A/Q_a + Q_B/Q_b = \text{Synergism Index (SI)}$$

where $Q_a$ and $Q_b$ are the quantities of compound A or B, acting alone, that produce an end point, and where $Q_A$ and $Q_B$ are the quantities of Compound A or B acting in the A/B mixture, that produce an endpoint. The endpoint is defined by the particular test method employed, as for example the ASTM standardized tests or the Minimum Inhibitory Concentration (MIC).

The performance of active ingredient mixtures will be described. Where the SI index is equal to 1, additivity exists; the performance of the ingredients in the mixture is equal to the sum of the individual performances. Where the SI index is greater than 1, antagonism exists; the performance of the ingredients is less than the sum of their individual performance. Where the performance of the mixture is greater than the sum of the individual performance, synergism exists and SI is less than 1.

EXPERIMENTAL EVALUATIONS

Table 1 discloses the synergistic combinations of BNEF and BNPD for specific microorganisms used in water treatment application. The method used for this study was a minimum inhibitory concentration analyses in an appropriate growth medium. Pure cultures of the microorganisms were obtained from the American Type Culture Collection (ATCC). Each organism was grown in nutrient-rich media recommended by ATCC. Sterile media was then inoculated with the test organism and a dose of one or both antimicrobials. The minimum inhibitory concentration (MIC) of BNEF and BNPD used separately was first determined. Then, a wide range of BNEF/BNPD combinations were tested systematically until synergistic compositions were discovered. The endpoint is the lowest concentration of antimicrobial tested which completely inhibited the growth of the microorganism for up to 48 hours of incubation. The compositions which were synergistic are listed in Table 1.

TABLE 1

ATTACHMENT "A"

| Microorganism | Concentrations (ppm) A.a - BNEF: B.b = BNPD | | | | |
|---|---|---|---|---|---|
| | $Q_a$ | $Q_b$ | $Q_A$ | $Q_B$ | SI |
| *Pseudomonas aeruginosa* | 12.5 | 12.5 | 0.8 | 6.2 | 0.56 |
| | | | 1.6 | 6.2 | 0.63 |
| | | | 3.1 | 3.1 | 0.50 |
| | | | 3.1 | 6.2 | 0.75 |
| | | | 6.2 | 1.6 | 0.63 |
| *Enterococcus faecalis* | >50 | 31.2 | 1.6 | 15.6 | 0.53 |
| | | | 3.1 | 15.6 | 0.56 |
| | | | 6.2 | 15.6 | 0.62 |
| | | | 12.5 | 7.8 | 0.50 |
| *Bacillus subtilis* | 3.3 | 6.5 | 0.41 | 3.30 | 0.63 |
| | | | 0.81 | 1.63 | 0.50 |
| | | | 1.60 | 0.81 | 0.61 |
| *Staphylococcus aureus* | 4.7 | 12.5 | 2.30 | 1.60 | 0.81 |
| | | | 1.20 | 3.10 | 0.50 |
| | | | 0.59 | 6.30 | 0.63 |
| *Aspergillus niger* | 3.1 | 312.0 | 0.4 | 156.0 | 0.63 |
| *Candida albicans* | 1.6 | 312.0 | 0.4 | 156.0 | 0.76 |

TABLE 1-continued
ATTACHMENT "A"

| Microorganism | Concentrations (ppm) A.a - BNEF: B.b = BNPD | | | | |
|---|---|---|---|---|---|
| | $Q_a$ | $Q_b$ | $Q_A$ | $Q_B$ | SI |
| Chlorella pyrenoidosa | 0.5 | 8.0 | 0.25 | 2.0 | 0.75 |
| | | | 0.125 | 2.0 | 0.50 |
| Anabaena | 1 | 8 | 0.5 | 2 | 0.75 |
| | | | 0.25 | 4 | 0.75 |
| Chaetomium | 1.5 | 250 | 0.38 | 125 | 0.75 |
| Chlamydomonas | 0.78 | 50 | 0.39 | 12.5 | 0.75 |
| Schizothrix | 1.5 | 6.25 | 0.78 | 1.56 | 0.75 |
| | | | 0.39 | 3.1 | 0.75 |
| | | | 0.78 | 0.78 | 0.62 |

The synergistic ratio of BNEF to BNPD based upon the data in Table 1 is about 1:0.25 to 1:390, depending upon the particular test.

Table 2 shows the synergistic combinations of BNEF and BNPD in standardized water treatment applications tests. Each test method is described in detail by the American Society for Testing and Materials (ASTM) and can be found in literature.

Table 2 that the synergistic ratio of BNEF to BNPD ranges from about 1:0.4 to about 1:200 1:05 to about 1:400 depending upon the particular test.

FIG. 1 illustrates the results o chemical stability tests performed to determine a practical BNEF/BNPD concentrate in a liquid carrier. As an example, a stable composition of BNEF and BNPD in tetrahydrofurfuryl alcohol is disclosed. At 0° and 25° Celsius, there was essentially no loss in active ingredients even after over 210 days storage. At 50° C, there was a decline in the concentration of active ingredients but even after over 200 days, less than 20% of the active ingredients were lost. This is significant since the 50° C. storage condition is very drastic. Less than 10% loss of active ingredient after 30 days at 50° C. is considered acceptable for practical applications of the product.

What is claimed is:

1. A synergistic composition for use as an antimicrobial for inhibiting microbial growth selected from the group consisting of algae, fungi, bacteria and yeast in an aqueous media commmprising 2-(2-bromo-2-nitroethenyl) furan ("BNEF") and 2-bromo-2-nitropropane -1,3-diol ("BNPD").

2. A synergistic composition as claimed in claim 1 wherein the weight ratio of BNEF to BNPD is in the range of 1:0.25 to 1:400.

3. A method for inhibiting microbial growth selected from the group consisting of algae, fungi, bacteria and yeast in an aqueous media which comprises adding thereto and antimicrobially effective amount of the synergistic composition comprising of 2-(2-brommo-2-nitroethenyl)furan ("BNEF") and 2-bromo-2-nitropro-ane-1, 3-diol ("BNPD"), wherein the weight ratio of BNEF to BNPD is in the range of 1:0.25 to 1:400.

4. A method as claimed in claim 3 wherein the bacterium is selected from the group consisting of Gram positive bacteria, Gram negative bacteria, aerobic bacteria, anaerobic bacteria, sulfate reducing, bacteria iron oxidizing bacteria and cyanobacteria.

5. A method as claimed in claim 3 wherein the aqueous media is selected from the group consisting of pulp and paper process flow, wood preservatives, evaporative cooling waters, water systems, air-washers, metal-working fluids, cosmetics, toiletries, acrylic latex paints, emulsions, adhesives, coatings, oilfield injection water and drilling muds, swimming pools and spas, and institutional hard-surface disinfection.

6. A method as claimed in claim 3 wherein the bacterium is *Pseudomonas aeruginosa*.

7. A method as claimed in claim 3 wherein the bacterium is *Enterococcus faecalis*.

8. A method as claimed in claim 3 wherein the bacterium is *Bacillus subtilis*.

9. A method as claimed in claim 3 wherein the bacterium is *Staphylococcus aureus*.

10. A method as claimed in claim 3 wherein the fungi is *Aspergillus niger*.

11. A method as claimed in claim 3 wherein the yeast is *Candida albicans*.

12. A method as claimed in claim 3 wherein the algae is *Chlorella pyrenoidosa*.

13. An antimicrobial composition for inhibiting microbial growth selected from the group consisting of algae, fungi, bacteria and yeast in an aqueous media comprising a synergistic mixture of 2-(2-Bromo-2-nitro-ethenyl)furan ("BNEF") and 2-Bromo-2-nitropropane-1,3-diol ("BNPD"), wherein the weight ratio of BNEF to BNPD is in the range of 1:0.05 to 1:400 and a carrier chosen from the group consisting of tetrahydrofurfuryl alcohol, N-methyl pyrrolidone or dimethylformamide in liquid form.

14. A composition as claimed in claim 13 wherein the carrier is tetrahydrofurfuryl alcohol.

15. A composition as claimed in claim 13 wherein the carrier is N-methyl pyrrolidone.

16. A composition as claimed in claim 13 wherein the composition comprises 20% w/v of the synergistic mixture of BNEF and BNPD and 80% w/v of carrier in liquid form.

17. A composition as claimed in claim 14 wherein the carrier is dimethylformamide.

* * * * *